United States Patent [19]

Berges

[11] 4,174,324

[45] Nov. 13, 1979

[54] 3-(CARBOXYMETHYL)THIO-1H-1,2,4-TRIAZOL-5-THIONE

[75] Inventor: David A. Berges, Wayne, Pa.

[73] Assignee: Smithkline Corporation, Philadelphia, Pa.

[21] Appl. No.: 921,922

[22] Filed: Jul. 3, 1978

Related U.S. Application Data

[62] Division of Ser. No. 811,642, Jun. 30, 1977, Pat. No. 4,117,124.

[51] Int. Cl.$^2$ .............................................. C07D 249/12
[52] U.S. Cl. .................................................. 548/264
[58] Field of Search ....................... 260/308 R, 308 C

[56] References Cited

U.S. PATENT DOCUMENTS

| | | | |
|---|---|---|---|
| 3,701,784 | 10/1972 | Seidel et al. | 260/308 R |
| 3,989,694 | 11/1976 | Berges | 260/308 R |
| 4,113,944 | 9/1978 | Kai et al. | 260/308 C |
| 4,128,722 | 12/1978 | Berges | 260/308 R |

FOREIGN PATENT DOCUMENTS 760181  10/1956  United Kingdom .............. 260/302 SD

*Primary Examiner*—Alton D. Rollins
*Attorney, Agent, or Firm*—Joseph A. Marlino; Richard D. Foggio; William H. Edgerton

[57] ABSTRACT

Novel cephalosporins having various acyl substituents at the 7-position and a carboxymethylthio substituted triazolylthiomethyl group at the 3-position of the cephem nucleus are prepared. These compounds have antibacterial activity.

3 Claims, No Drawings

3-(CARBOXYMETHYL)THIO-1H-1,2,4-TRIAZOL-5-THIONE

This is a division of application of Ser. No. 811,642 filed June 30, 1977, now U.S. Pat. No. 4,117,124.

This invention relates to a new series of cephalosporin compounds having antibacterial activity and to intermediates useful for preparing them. The structures of the new compounds are characterized by having at the 3-position a carboxymethylthio substituted triazole group.

Exemplary of the compounds of this invention are those represented by the following structural formula:

Exemplary of the compounds of this invention are those represented by the following structural formula:

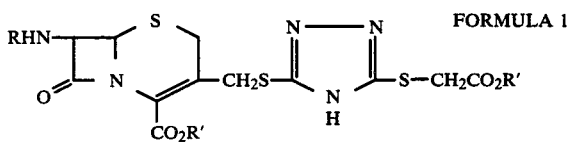

FORMULA 1 in which R represents a pharmaceutically acceptable acyl group known to be of utility as a substituent on the 7-amino group in the structures of known or prior art cephalosporins or on the 6-amino group in the structures of known or prior art penicillins.

Representative acyl substituents are:

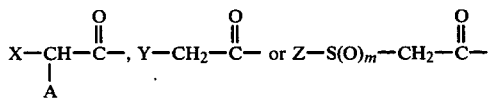

wherein:

X is thienyl, furyl, phenyl or phenyl monosubstituted with hydroxy, hydroxymethyl, formamido or ureido;

A is $NH_2$, OH, COOH, $SO_3H$, formyloxy or, when the α-C-hydrogen is absent, methoxyimino;

Y is cyano, sydnone, pyridone, thienyl, o-aminomethylphenyl, phenyl or tetrazolyl;

Z is methyl, trifluoromethyl, trifluoroethyl, pyridyl or cyanomethyl; and m is zero to two;

R' is hydrogen or an alkali metal salt such as sodium or potassium.

Each of the three partial structures above represent subgeneric groups of compounds covered by this invention.

Representative 7-acylamino substituents of the compounds of Formula 1 are listed below:
α-hydroxyphenylacetamido
α-aminophenylacetamido
α-amino-4-hydroxyphenylacetamido
trifluoromethylthioacetamido
2,2,2-trifluoroethylsulfinylacetamido
2,2,2-trifluoroethylthioacetamido
cyanoacetamido
α-carboxythienylacetamido
α-carboxyphenylacetamido
α-sulfophenylacetamido
methylsulfonylacetamido
cyanomethylthioacetamido
3-sydnoneacetamido
1-tetrazolylacetamido
2-thienylacetamido
α(Z)-(methoxyimino)-2-furanacetamido
4-pyridylthioacetamido
o-aminomethylphenylacetamido Others together with N-acylation procedures may be found in *Cephalosporins and Penicillins*, Flynn, Academic Press, 1972; U.S. Pat. Nos. 2,721,196 and 3,953,424; Belgian Pat. No. 832,725; German Pat. Nos. 2,127,285 and 2,406,165.

It will be recognized that the 4-carboxylic acid group of the compounds of Formula 1 may be readily esterified by methods well known to the art. These esters include, for example, simple alkyl and aryl esters as well as esters which are easily cleaved, within the body, to the parent acid such as indanyl, pivaloyloxymethyl, acetoxymethyl, propionyloxymethyl, glycyloxymethyl, phenylglycyloxymethyl and thienylglycyloxymethyl esters and others. Of course, when A is COOH, this group may be similarly esterified. All such ester derivatives are included within the scope of this invention.

Also covered in this invention are the pharmaceutically accceptable, nontoxic derivatives of compounds of compoundsof Formula 1 from which they derive utility: the salts, as stated above easily split ester or ether derivatives of either a carboxy or hydroxy function, amide derivatives at an amino group contained in a 7-phenylglycylamino group, for example, the furyl-, pyranyl-, oxolanyl- or oxiranylcarbonyl amides (i.e. Belgian Pat. No. 835,295), the solvates such as hydrates, glycolates or alcoholates. As examples of these, one skilled in the art would be able to prepare and use the alkali metal salts such as the sodium or potassium salts (for example using sodium or potassium 2-ethyl hexanoate), ammonium salts, organic amine salts such as those with procaine or dibenzylethylenediamine.

Other known cephalosporin modifications can be made by known synthetic procedures such as introduction of an α-methoxy group at position 7, preferably at the stage of the 7-aminocephalosporanic acid reactants disclosed below (IV), prior to N-acylation. Optical isomers are also possible such as with the mandeloyl or phenylglycyl substituents at 7. The D-forms of these subgeneric groups are preferred.

The compounds of this invention are most conveniently prepared by a displacement of the acetoxy group of a known 7-acylaminocephalosporanic acid (II) by [(4,5-dihydro-5-thioxo-1H-1,2,4-triazol-3-yl)thio]acetic acid (III). Alternatively a similar displacement with the above acetic acid can be run on 7-aminocephalosporanic acid to give 7-amino-3-[[3-(carboxymethyl)thio-1H-1,2,4-triazol-5-yl]-thiomethyl]-3-cephem-4-carboxylic acid (IV) which may then be N-acylated as known to the art as described above. Suitable protective groups may be used in either method as is known to the art (see "Protective Groups in Organic Chemistry", J. F. W. McOmie, Plenum Press, 1973, Chapters 2 and 3 for use of amino, carboxy, sulfo or hydroxyl protective groups).

For example, the t-butyl (for COOH) or t-butoxycarbonyl (for $NH_2$) groups are easily removed by treatment with trifluoroacetic acid.

The carboxymethylthio substituted triazole, which may exist in several tautomeric forms, and is here expressed by Formula III, is a new compound and is part of this invention.

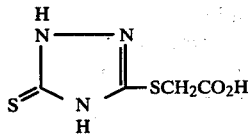

III

The invention also includes the alkali metal and ammonium salts of the compound of Formula III.

The compounds of Formula I have antibacterial activity against both Gram positive and Gram negative bacteria with minimum inhibitory concentrations (MIC's) in vitro from 0.2 to greater than 200 μg/ml. Test results for 7-D-mandelamido-3-[[3-(carboxymethyl)thio-1$\underline{H}$-1,2,4-triazol-5-yl]thiomethyl]-3-cephem-4-carboxylic acid, disodium salt, hydrate (A) are:

|  | A | Cephalothin | Cefazolin |
|---|---|---|---|
| S. aureus HH 127 | 1.6 | 0.4 | 0.4 |
| S. aureus SK 23390 | 0.8 | 0.2 | 0.4 |
| S. aureus villaluz SK 70390 | >200 | 50 | 200 |
| Strep. faecalis HH 34358 | 100 | 12.5 | 6.3 |
| E. coli SK 12140 | 0.8 | 3.1 | 1.6 |
| E. coli HH 33779 | 0.8 | 6.3 | 1.6 |
| Kleb. pneumo. SK 4200 | 0.4 | 3.1 | 1.6 |
| Kleb. pneumo. SK 1200 | 0.2 | 1.6 | 0.8 |
| Salmonella ATCC 12176 | 0.8 | 1.6 | 0.8 |
| Pseudo. aeru. HH 63 | >200 | 200 | >200 |
| Serratia marc. ATCC 13880 | 12.5 | >200 | >200 |
| Proteus morgani 179 | 1.6 | >200 | 200 |
| Entero. aerog. ATCC 13048 | 1.6 | 12.5 | 1.6 |
| Entero. cloacae HH 31254 | 0.8 | 6.3 | 0.8 |

Compound A gave an $ED_{50}$ in mice of 1.56 against E. coli as well as 1.02 mg/kg against Kleb. pneumo. (s.c.).

These results are superior to those for a related compound, 7-D-mandelamido-3-(2-carboxymethylthio-1,3,4-thiadiazol-5-yl-thiomethyl)-3-cephem-4-carboxylic acid, sodium salt hydrate which gave an $ED_{50}$ against E. coli of 6.4 and as well as 4.4 mg/kg against Kleb. pneumo.

Pharmaceutical compositions having antibacterial activity which comprise a pharmaceutical carrier containing an active but nontoxic quantity of a compound of Formula 1 as well as methods of combatting bacterial infections by administering such a composition to an infected animal or human host in a nontoxic amount sufficient to combat such infections are also objects of this invention. The administration may be orally or by parenteral injection such as subcutaneously, intramuscularly or intravenously. The injection of suitably prepared sterile solutions or suspensions containing an effective, nontoxic amount of the new cephalosporin compound is the preferred route of administration.

The compounds of Formula 1 are formulated and administered in the same manner as other prior art cephalosporins such as cephazolin of cephalothin. The dosage regimen comprises administration, preferably by injection, of an active but nontoxic quantity of a compound of Formula 1 selected from the dosage unit range of from about 250 mg. to 600 mg. with the total daily dosage regimen being from about 750 mg. to 6 g. The precise dosages are dependent upon the age and weight of the subject and on the susceptibility of the infection being treated to each individual. These can be determined by those skilled in the art based on the data disclosed herein compared with that available to the art attained with the known cephalosporins outlined herebefore.

The following examples illustrate the invention but are not to be construed as limiting the scope thereof. Temperatures are in degrees Centigrade (° C.) unless otherwise stated.

EXAMPLE 1

To a suspension of 5.48 g. (40 mmol) of 1,2,4-triazolidine-3,5-dithione, monohydrazine salt in 80 ml. of tetrahydrofuran and 80 ml. of dimethylformamide was added a solution of 6.7 (40 mmol) of ethyl bromoacetate in 20 ml. of tetrahydrofuran. The mixture was stirred at room temperature for 1½ hours, and then at 50° C. for ½ hour. The solution was filtered and the filtrate was concentrated to 80 ml., diluted with 250 ml. of water and extracted with diethyl ether. The extract was dried ($MgSO_4$) and evaporated to dryness to give a residue which was crystallized from methanol and water to give 5.76 g. (65% yield) of ethyl [(4,5-dihydro-5-thioxo-1$\underline{H}$-1,2,4-triazol-3-yl)thio]acetate. mp 134°–6° C.

A solution of 2.19 g. (10 mmol) of ethyl [(4,5-dihydro-5-thioxo-1$\underline{H}$-1,2,4-triazol-3-yl)thio]acetate in 50 ml. of 5% sodium hydroxide was heated at reflux for 1 hour. After thorough cooling, the mixture was filtered, and the filtrate was washed with ethyl acetate. The aqueous layer was separated, acidified to pH 1 and extracted with ethyl acetate. The extract was evaporated in vacuo to dryness. The residue was crystallized from chloroform to give 1.43 g. (75% yield) of [(4,5-dihydro-5-thioxo-1$\underline{H}$-1,2,4-triazol-3-yl)thio]acetic acid.

To a solution of 1.16 g. (13.8 mmol) of sodium bicarbonate in 30 ml. of water was added 1.32 g. (6.9 mmol) of [(4,5-dihydro-5-thioxo-1$\underline{H}$-1,2,4-triazol-3-yl)thio]acetic acid. After $CO_2$ gas evolution had ceased, 2.12 g. (5 mmol) of 7-mandelamido-cephalosporanic acid sodium salt was added to the solution. The mixture was heated at 80° C. for 3.5 hours. After cooling, the solution was filtered. The filtrate was applied to an XAD-7 (200 ml.) resin column, eluting with water. The fractions containing product by thin layer chromatography were pooled and evaporated to dryness. The residue was triturated with absolute ethanol and filtered. The filtrate was diluted with isopropanol, and the solid formed was filtered, air-dried, dissolved in de-ionized water and lyophilized to give 1.02 g. (15.6 % yield) of 7-O-mandelamido-3-[[3-(carboxymethyl)thio-1$\underline{H}$-1,2,4-triazol-5-yl]thiomethyl]-3-cephem-4-carboxylic acid, disodium salt hydrate, mp 220°–230° C. dec. Anal. calculated for $C_{20}H_{17}N_5O_7S_3Na_2.4H_2O$=C, 36.75; H, 3.85; N, 10.71. Found: C, 36.47; H, 3.53; N, 10.11. IR-(NUJOL)=5.65 μ.

EXAMPLE 2

An aqueous solution (100 ml.) of 4.27 g. (0.0096 mol) of 7-[α(Z)-(methoxyimino)-2-furanacetamido]cephalosporanic acid sodium salt, 1.78 g. (0.0212 mol) of sodium bicarbonate and 2.02 g. (0.0106 mol) of [(4,5-dihydro-5-thioxo-1$\underline{H}$-1,2,4-triazol-3-yl)thio]acetic acid is heated at 65° C. for 6 hours during which time the pH is maintained at 7.6-7.8 with dilute sodium bicarbonate. After cooling, the reaction mixture is purified on an XAD-7 column as described in Example 1 to give a lyophilized product. 7-[α(Z)-(methoxyimino)-2-furanacetamido]-3-[[3-(carboxymethyl)thio-1$\underline{H}$-1,2,4-triazol-5-yl]thiomethyl]-3-cephem-4-carboxylic acid, disodium salt.

EXAMPLE 3

A mixture of 5.22 g. (10.0 mmol) of 7-(D-α-t-butoxycarbonylamino-4-hydroxyphenylacetamido)cephalosporanic acid and an excess (15.0 mmol) of [(4,5-dihydro-5-thioxo-1H-1,2,4-triazol-3-yl)thio]acetic acid in 75 ml. of pH 6.4 phosphate buffer solution is treated with sufficient sodium bicarbonate to give a pH of 6.4. The mixture is heated at 70° for 3 hours, cooled, acidified with dilute hydrochloric acid to pH 2 and extracted with ethyl acetate. Removal of the ethyl acetate in vacuo give the t-boc derivative of the desired compound. This derivative is stirred at 25° C. with 25 ml. of trifluoroacetic acid and 25 ml. of 1,3-dimethoxybenzene for 2 hours. The mixture is evaporated to dryness in vacuo, ethyl acetate is added to the residue and the precipitated salt is collected. This is dissolved in water and treated with Amberlite IR-45 weakly basic ion-exchange resin. The solution is lyophilized to give 7-(D-α-amino-4-hydroxyphenylacetamido)-3-[[3-carboxymethyl)thio-1H-1,2,4-triazol-5-yl]thiomethyl]-3-cephem-4-carboxylic acid. Similar treatment of the t-boc derivatives of the 7-DL-(α-aminophenylacetamido)cephalosporanic acid gives the corresponding 7-DL-(α-aminophenylacetamido)-3-[[3-carboxymethyl)thio-1H-1,2,4-triazol-5-yl]thiomethyl]-3-cephem-4-carboxylic acid.

EXAMPLE 4

A mixture of an excess (12.2 mmol) of [(4,5-dihydro-5-thioxo-1H-1,2,4-triazol-3-yl)thio]acetic acid, 32.5 mmol of sodium bicarbonate and 8.1 mmol of 7-trifluoromethylthioacetamidocephalosporanic acid in 50 ml. of water is stirred at 70° for 5 hours. The reaction mixture is cooled and applied to an XAD-2 column and eluted with water and then methanol. The product-containing effluent is evaporated to dryness to give a residue which is dissolved in a small amount of water and lyophiized to give 7-trifluoromethylthioacetamindo-3-[[3-(carboxymethyl)thio-1H-1,2,4-triazol-5-yl]thiomethyl]-3-cephem-4-carboxylic acid disodium salt. Substituting 7-(2-thienylacetamido)-cephalosporanic acid gives 7-(2-thienylacetamido)-3-[[3-(carboxymethyl)thio-1H-1,2,4-triazol-5-yl]thiomethyl]-3-cephem-4-carboxylic acid disodium salt.

Stoichiometric quantities of cephalosporanic acids having the individual 7-acylamino substituent listed hereabove may be substituted in Examples 1–3 with variations which will be obvious to those skilled in this art.

EXAMPLE 5

An injectable pharmaceutical composition is formed by adding sterile saline solution (2 ml.) to 500 mg. of the product of Example 1. This material is injected parenterally four times daily to a human patient infected with susceptible bacteria. Other compounds of this invention may be similarly used.

What is claimed is:

1. [(4,5-Dihydro-5-thioxo-1H-1,2,4-triazol-3-yl)thio]acetic acid and its alkali metal and ammonium salts.

2. The compound of claim 1 being [(4,5-dihydro-5-thioxo-1H-1,2,4-triazol-3-yl)thio]acetic acid.

3. The compound of claim 1 being the sodium salt.

* * * * *